US00PP29794P2

(12) United States Plant Patent
Nelson et al.

(10) Patent No.: US PP29,794 P2
(45) Date of Patent: Nov. 6, 2018

(54) STRAWBERRY PLANT NAMED 'INSPIRE'

(50) Latin Name: *Fragaria ananassa*
Varietal Denomination: INSPIRE

(71) Applicant: Berry Genetics, Inc., Freedom, CA (US)

(72) Inventors: Steven D. Nelson, Watsonville, CA (US); Michael D. Nelson, Watsonville, CA (US); Leo W. Stoeckle, Moorpark, CA (US); Daniel S. Nelson, Watsonville, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 15/732,143

(22) Filed: Sep. 26, 2017

(51) Int. Cl.
*A01H 5/08* (2018.01)

(52) U.S. Cl.
USPC ..... Plt./209

(58) Field of Classification Search
USPC ..... Plt./209
See application file for complete search history.

*Primary Examiner* — Annette H Para
(74) *Attorney, Agent, or Firm* — Foley & Lardner LLP

(57) ABSTRACT

This invention relates to a new and distinct variety of strawberry plant named 'INSPIRE'. This new strawberry plant named 'INSPIRE' is primarily adapted to the growing conditions of the central coast of California, and is primarily characterized by its orange red fruit color; very firm fruit flesh; very smooth, even fruit surface, with very little difference in shape between primary and secondary fruit; medium fruit size that is much longer than broad; excellent fruit flavor; and medium plant size.

4 Drawing Sheets

BACKGROUND OF THE INVENTION

The present invention relates to a new and distinct strawberry variety named 'INSPIRE'. This new variety is a result of a controlled cross made in 2009 in an ongoing breeding program between strawberry variety designated 'BG-1975' (U.S. Plant Pat. No. 17,725) as the seed (female) parent, and strawberry variety designated 'Primori' as the pollen (male) parent. The variety is botanically known as *Fragaria ananassa.*

The seedling resulting from the aforementioned cross was selected from a controlled breeding plot in Ventura County, Calif. in the winter of 2011. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'INSPIRE' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'INSPIRE', which in combination distinguish this strawberry plant as a new and distinct variety:

1. Orange red fruit color;
2. Very firm fruit flesh;

3. Very smooth, even fruit surface, with very little difference in shape between primary and secondary fruit;
4. Medium fruit size that is much longer than broad;
5. Excellent fruit flavor; and
6. Medium plant size.

The strawberry variety that is believed to be most closely related to the new variety 'INSPIRE' is 'BG-959' (U.S. Plant Pat. No. 17,864). In side-by-side comparisons to the similar strawberry variety 'BG-959', 'INSPIRE' differs by the following combination of characteristics as described in Table 1.

TABLE 1

| Characteristic | 'INSPIRE' | 'BG-959' (U.S. Plant Pat. No. 17,864) |
|---|---|---|
| Fruit: color | Orange red | Red |
| Fruit: firmness of flesh | Very firm | Firm |
| Fruit: expression of hollow center | Weak | Strong |
| Fruit: difference between primary and secondary | None or very slight | Moderate |
| Fruit: flavor | Excellent | Good |
| Plant: size | Medium | Small |
| Terminal leaf: shape of base | Acute | Obtuse |
| Foliage: color | Medium green | Ranges from medium to dark green |
| Stipule: anthocyanin intensity | Absent or very weak | Strong |
| Flowers: position relative to foliage | Above | Level with |

For identification, a series of molecular markers have been determined for this new variety.

'INSPIRE' differs from its parents, 'BG-1975' and 'Primori' by the following combination of characteristics as described in Tables 2 and 3.

TABLE 2

| Characteristic | 'INSPIRE' | 'BG-1975' (U.S. Plant Pat. No. 17,725) |
|---|---|---|
| Fruit: color | Orange red | Orange |
| Fruit: firmness of flesh | Very firm | Firm |
| Fruit: shape | Conical (much longer than broad) | Conical (slightly longer than broad) |
| Fruit: insertion of achenes | Level with the surface | Below the surface |
| Marketable yield | Ranges from medium to low | Medium |

TABLE 3

| Characteristic | 'INSPIRE' | 'Primori' |
|---|---|---|
| Fruit: size | Medium | Ranges from medium to small |
| Fruit: glossiness | Strong | Medium |
| Fruit: attitude of sepals | Ranges from outward to upward | Outward |
| Fruit: flavor | Excellent | Good |

BRIEF DESCRIPTIONS OF THE PHOTOGRAPHS

The accompanying color photographs illustrate the overall appearance of typical specimens of the new strawberry variety 'INSPIRE' at various stages of development, as true as it is reasonably possible with color reproductions of this type. Color in the photographs may differ slightly from the color value cited in the botanical descriptions which accurately describe the color of 'INSPIRE'. The depicted plant and plant parts of the new strawberry variety 'INSPIRE' are approximately six months old. The photographs were taken in Ventura County, Calif.

DETAILED BOTANICAL DESCRIPTION

Figure 1:
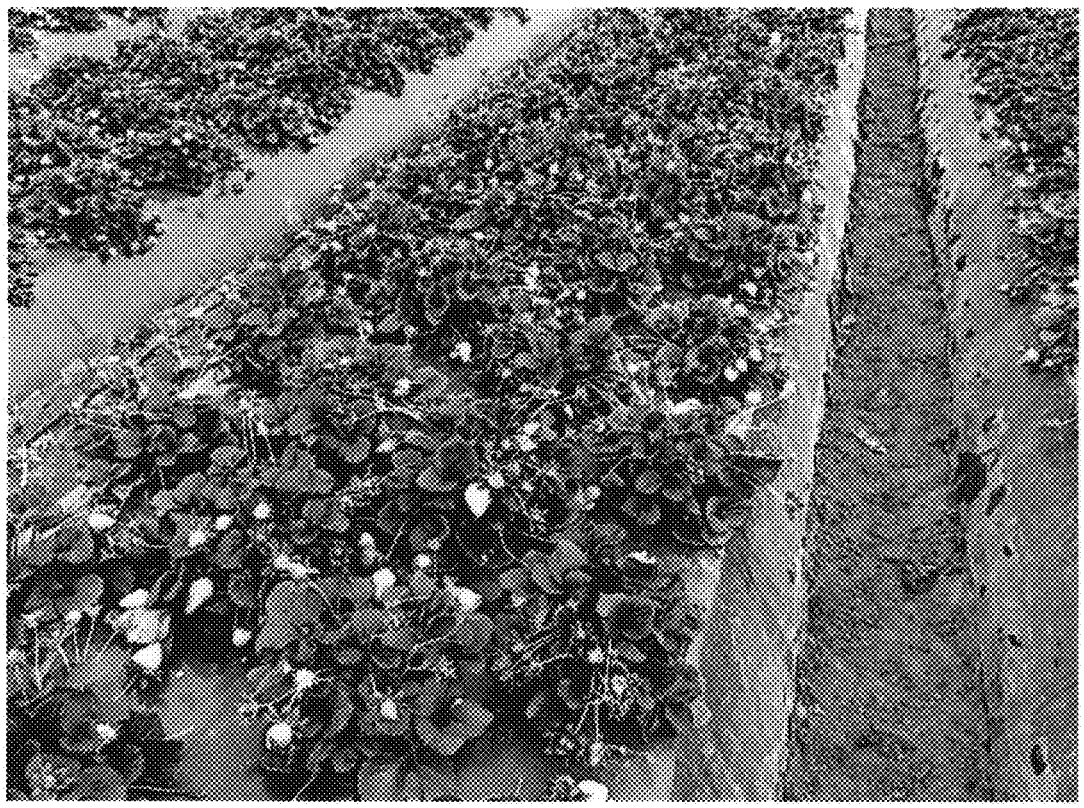
FIG. 1 shows typical fruiting field characteristics of 'INSPIRE', taken in the month of March.
Figure 2:
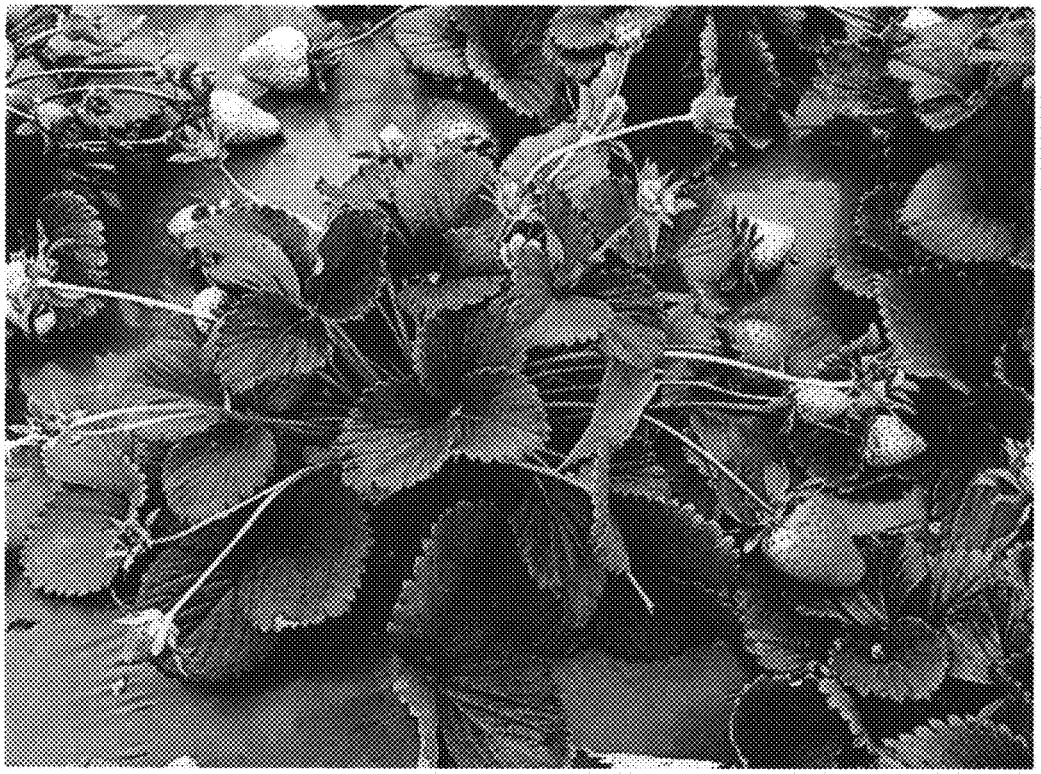
FIG. 2 shows a close-up view of a typical plant of 'INSPIRE', taken in the month of March.
Figure 3:
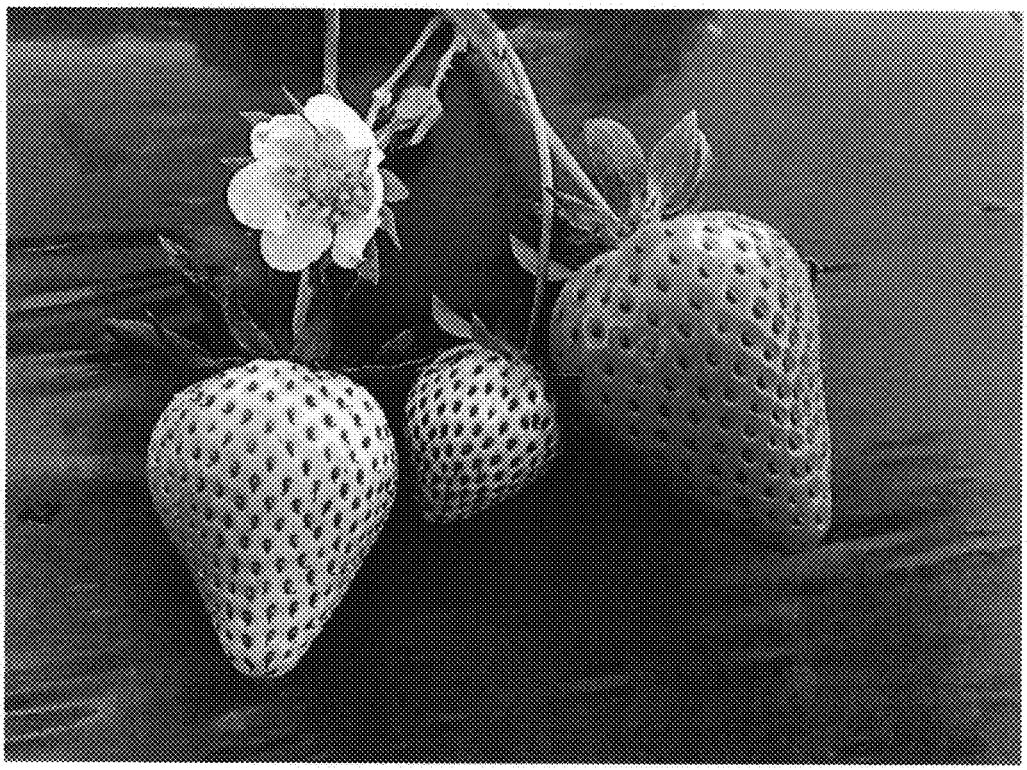
FIG. 3 shows typical mature and immature field fruit of 'INSPIRE', taken in the month of March.
Figure 4:
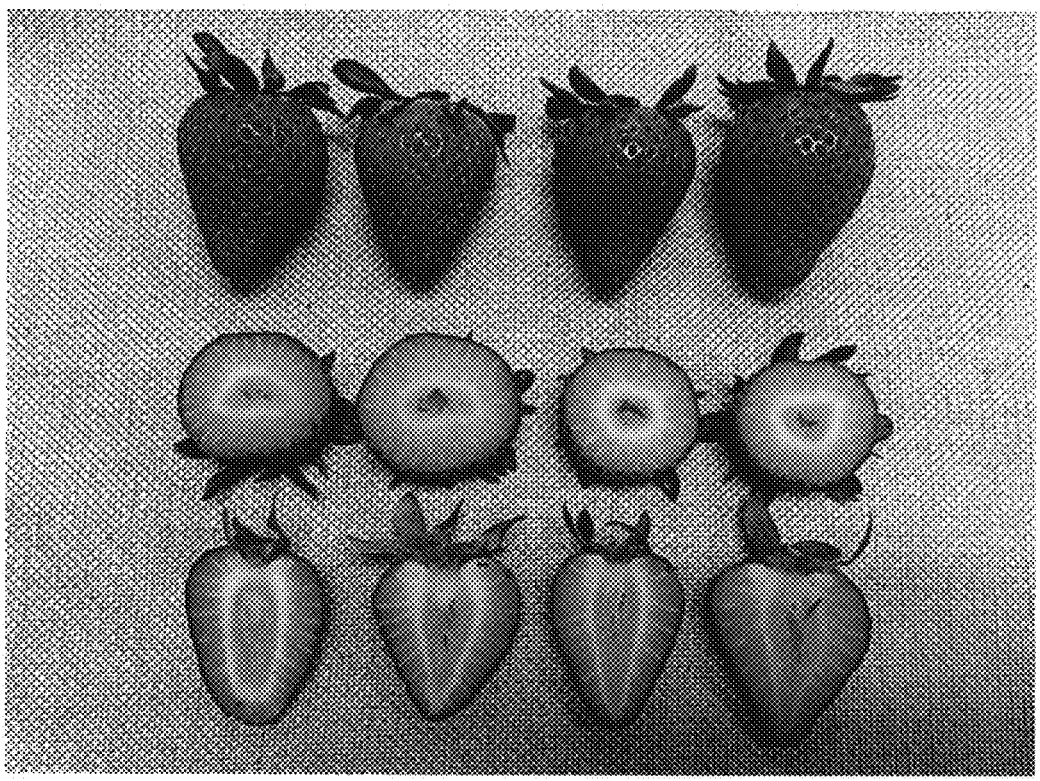
FIG. 4 shows typical internal and external mature fruit characteristics of 'INSPIRE', taken in the month of March.

The new variety 'INSPIRE' has not been observed under all possible environmental conditions. The characteristics of the new variety 'INSPIRE' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'INSPIRE', unless otherwise noted, are based on observations taken during the 2017 growing season in Ventura County, Calif. These measurements and ratings were taken from plants of 'INSPIRE' dug from a high-elevation nursery located in Siskiyou County, Calif. during early October 2016 and planted approximately four to five days later in Ventura County, Calif. The approximate age of the observed plants is six months. Yield observations including average weight and marketable yield, along with fruit quality characteristics including soluble solids, are averaged from four years of data collected from the 2014 through 2017 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'INSPIRE'.

Fruit characteristics:

*Color of mature fruit*.—RHS N34B (orange red).

*Color of internal flesh* (*excluding core*).—RHS 34C (light red).

*Color of core*.—RHS 39B (ranges from light red to medium red).

*Average length* (*cm*).—4.7.

*Average width* (*cm*).—3.7.

*Size*.—Medium.

*Average length/width ratio*.—1.26 (much longer than broad).

*Average calyx diameter* (*cm*).—5.2.

*Season average weight* (*gm*).—26.0.

*Achene color, shaded side*.—RHS 153A (yellow green group).

*Achene color, sun-exposed side*.—RHS 184A (greyed purple group).

*Average achene weight* (*mg*).—0.52.

*Average achenes per berry*.—354.

*Season marketable yield* (*gm/plant*).—866.

*Predominant shape*.—Conical.

*Difference in shape between primary and secondary fruit*.—None or very slight.

*Band without achenes*.—Narrow.

*Evenness of surface*.—Even or very slightly uneven.

*Evenness of color*.—Even or very slightly uneven.

*Glossiness*.—Strong.

*Insertion of achenes*.—Level with surface.

*Position of calyx attachment*.—Inserted.

*Attitude of sepals*.—Ranges from outward to upward.

*Size of calyx in relation to fruit diameter*.—Ranges from slightly larger to much larger.

*Adherence of calyx* (*when fully ripe*).—Strong.

*Firmness of flesh*.—Ranges from firm to very firm.

*Distribution of red color of the flesh*.—Marginal and central.

*Hollow center expression*.—Weak.

*Flavor*.—Excellent.

*Soluble solids* (% *Brix*).—8.3.

*Time of first flowering*.—Medium (Mid-December in Ventura County, Calif.).

*Time of first fruit*.—Medium (Mid-January in Ventura County, Calif.).

*Harvest period*.—January to May (in Ventura County, Calif.).

*Harvest maturity*.—Mid-season (March).

*Type of bearing*.—Not remontant.

Plant characteristics:
*Average height* (*cm*).—16.9.
*Average spread* (*cm*).—30.3.
*Size*.—Medium.
*Habit*.—Upright.
*Density*.—Medium.
*Vigor*.—Medium.
Stolon characteristics:
*Color*.—RHS 146C (yellow green group).
*Anthocyanin coloration*.—RHS 181B (greyed red group).
*Anthocyanin intensity*.—Medium.
*Pubescence*.—Medium.
*Attitude of hairs*.—Upward.
*Average quantity in nursery* (*per square foot*).—5 to 6 (medium).
*Average diameter at the bract* (*mm*).—2.9 (ranges from thin to medium).
Terminal leaflet characteristics:
*Average length* (*cm*).—6.2.
*Average width* (*cm*).—5.4.
*Average length/width ratio*.—1.15 (longer than broad).
*Shape of base*.—Acute.
*Margins* (*shape of teeth*).—Obtuse (serrate to crenate).
*Average serrations per leaf*.—21.9.
Foliage characteristics:
*Color of upper surface*.—RHS 137A (medium green).
*Color of underside*.—RHS 147B (yellow green group).
*Number of leaflets*.—3.
*Leaf size*.—Medium.
*Average length* (*cm*).—11.7.
*Average width* (*cm*).—10.0.
*Average area foliage* ($cm^2$).—116.8.
*Shape in cross section*.—Flat to slightly convex.
*Interveinal blistering*.—Medium.
*Leaf glossiness*.—Medium.
*Leaf variegation*.—Absent.
Petiole characteristics:
*Petiole color*.—RHS 144A (yellow green group).
*Average length* (*cm*).—10.2.
*Average diameter* (*mm*).—3.1.
*Petiolule color*.—RHS 144A (yellow green group).
*Petiolule average length* (*mm*).—7.8.
*Attitude of hairs*.—Strongly outward.
*Pubescence*.—Moderate.
Stipule characteristics:
*Color*.—RHS 146C (yellow green group).
*Anthocyanin coloration*.—RHS 56B (red group).
*Anthocyanin intensity*.—Absent or very weak.
*Average length* (*mm*).—17.2.
*Average width* (*mm*).—9.9.
Fruiting truss characteristics:
*Anthocyanin coloration*.—RHS 181C (greyed red group).
*Anthocyanin intensity*.—Medium.
*Average length at maturity* (*cm*).—24.0.
*Position relative to foliage*.—Above.
*Flower quantity* (*average per plant*).—40 to 50 (medium).
*Pedicel attitude of hairs*.—Upward.
*Pubescence*.—Weak.
*Attitude at first pick*.—Prostrate.
Flower characteristics:
*Petal color*.—RHS NN155C (white group).
*Sepal color*.—RHS 137B (green group).
*Corolla* (*flower*) *average diameter* (*mm*).—27.3 (medium).
*Calyx average diameter* (*mm*).—34.5.
*Petal average length* (*mm*).—10.8.
*Petal average width* (*mm*).—9.8.
*Petal average length/width ratio*.—1.11 (longer than broad).
*Average petals per flower*.—5.8.
*Sepal average length* (*mm*).—13.8.
*Sepal average width* (*mm*).—4.6.
*Sepal average length/width ratio*.—2.99.
*Average sepals per flower*.—11.6.
*Size of calyx relative to corolla*.—Larger.
*Size of inner calyx relative to outer calyx*.—Smaller.
*Relative position of petals* (*flowers with* 5 *or* 6 *petals*).—Ranges from touching to overlapping.
Reproductive organs:
*Receptacle color*.—RHS 147C (yellow green group).
*Pollen color*.—RHS 14A (yellow orange group).
*Stamen*.—Present.
*Pollen amount*.—Abundant.
Disease and pest reactions:
*Powdery mildew* (*Sphaerotheca macularis*).—Moderately resistant.
*Angular leaf spot* (*Xanthomonas fragariae*).—Moderately resistant.
*Botrytis fruit rot* (*Botrytis cinerea*).—Moderately susceptible.
*Fusarium wilt* (*Fusarium oxysporum*).—Susceptible.
*Anthracnose crown rot* (*Colletotrichum fragariae*).—Susceptible.
*Two-spotted spider mite* (*Tetranychus urticae*).—Moderately susceptible.

We claim:

1. A new and distinct strawberry plant named 'INSPIRE', as herein described and illustrated by the characteristics set forth above.

* * * * *